(12) United States Patent
Cornell et al.

(10) Patent No.: US 11,939,272 B2
(45) Date of Patent: Mar. 26, 2024

(54) COMPOSITION AND METHOD FOR GENERATING A SHADE GRADIENT IN ZIRCONIA DENTAL RESTORATION

(71) Applicant: Jensen Industries Inc., North Haven, CT (US)

(72) Inventors: Donald F. Cornell, Madison, CT (US); Yoonho Jun, Weatogue, CT (US)

(73) Assignee: JENSEN INDUSTRIES INC., North Haven, CT (US)

(*) Notice: Subject to any disclaimer, the term of this patent is extended or adjusted under 35 U.S.C. 154(b) by 393 days.

(21) Appl. No.: 16/358,050

(22) Filed: Mar. 19, 2019

(65) Prior Publication Data
US 2019/0284103 A1    Sep. 19, 2019

Related U.S. Application Data

(60) Provisional application No. 62/644,761, filed on Mar. 19, 2018, provisional application No. 62/748,884, filed on Oct. 22, 2018.

(51) Int. Cl.
| | | |
|---|---|---|
| *C04B 41/00* | (2006.01) | |
| *C04B 35/48* | (2006.01) | |
| *C04B 41/50* | (2006.01) | |
| *C04B 41/85* | (2006.01) | |

(52) U.S. Cl.
CPC ............ *C04B 41/009* (2013.01); *C04B 35/48* (2013.01); *C04B 41/5009* (2013.01); *C04B 41/5012* (2013.01); *C04B 41/85* (2013.01); *C04B 2235/3246* (2013.01); *C04B 2235/9661* (2013.01)

(58) Field of Classification Search
None
See application file for complete search history.

(56) References Cited

U.S. PATENT DOCUMENTS

| | | | | |
|---|---|---|---|---|
| 9,725,370 | B2* | 8/2017 | Jahns | C04B 41/52 |
| 9,962,247 | B2* | 5/2018 | Fujisaki | C04B 35/486 |
| 2014/0227654 | A1* | 8/2014 | Fujisaki | A61L 27/047 |
| | | | | 433/8 |
| 2015/0272833 | A1* | 10/2015 | Toriyabe | A61K 6/71 |
| | | | | 522/48 |
| 2015/0336853 | A1* | 11/2015 | Jahns | C04B 41/009 |
| | | | | 206/568 |
| 2017/0189143 | A1* | 7/2017 | Wolz | B05D 5/06 |
| 2017/0326645 | A1* | 11/2017 | Saito | B22F 10/20 |
| 2019/0388196 | A1* | 12/2019 | Kitamura | A61K 6/78 |
| 2020/0331807 | A1* | 10/2020 | Nonaka | A61C 13/0022 |
| 2021/0137655 | A1* | 5/2021 | Shen | A61K 6/818 |

FOREIGN PATENT DOCUMENTS

EP    3132788 A1    2/2017

* cited by examiner

*Primary Examiner* — Joseph D Anthony
(74) *Attorney, Agent, or Firm* — Troutman Pepper Hamilton Sanders LLP

(57) ABSTRACT

Disclosed are compositions and methods for bleaching and optionally coloring a shaded zirconia, particularly monochromatic pre-shaded dental zirconia. The compositions and methods are useful in generating a shade gradient in milled dental restorations. The compositions comprise metal salts or complex dissolved in a solvent.

6 Claims, 3 Drawing Sheets

FIG. 2

| Ex. | metal | zirconia | salt/complex | Conc. (wt%) | # coats | Bleaching | Warping (%) | Flexural Strength (MPa) | % Flex strength vs. control |
|---|---|---|---|---|---|---|---|---|---|
| 1 | control | 3Y | - | - | - | - | 0.34 | 1011 | 100% |
| 2 | yttrium (Blue X) | 3Y | $Y(NO_3)_3 \cdot 6H_2O$ | 50 – 70 | 2 | yes | 6.02 | 717 | 71% |
| 3 | magnesium | 3Y | $MgCl_2 \cdot 6H_2O$ | 50 | 2 | yes | - | 418.7 | 41% |
| 4 | zinc | 3Y | $ZnCl_2$ | 10 | 2 | yes | 1.01 | 1099 | 109% |
| 5 | zinc | 3Y | $Zn(NO_3)_2 \cdot 6H_2O$ | 10 | 2 | yes | 1.44 | 1023 | 101% |
| 6 | ytterbium | 3Y | $Yb(NO_3)_3 \cdot 5H_2O$ | 40 | 2 | no | 1.68 | - | |
| 7 | gadolinium | 3Y | $Gd(NO_3)_3 \cdot 6H_2O$ | 40 | 2 | no | 2.01 | - | |
| 8 | lanthanum | 3Y | $La(NO_3)_3 \cdot 6H_2O$ | 40 | 2 | no | - | - | |
| 9 | gallium | 3Y | $Ga(NO_3)_3 \cdot xH_2O$ | 10 | 2 | yes | 5.70 | 989 | 98% |
| 10 | aluminum | 3Y | $Al(NO_3)_3 \cdot 9H_2O$ | 10 | 1 | yes | - | 1052 | 104% |
| 11 | aluminum | 3Y | $Al(NO_3)_3 \cdot 9H_2O$ | 10 | 2 | yes | 1.23 | 1128 | 112% |
| 12 | aluminum | 3Y | $Al(NO_3)_3 \cdot 9H_2O$ | 10 | 3 | yes | - | 1126 | 111% |
| 13 | untreated | 5Y | - | - | - | - | - | 643 | 100% |
| 14 | aluminum | 5Y | $Al(NO_3)_3 \cdot 9H_2O$ | 10 | 2 | yes | - | 656 | 102% |
| 15 | aluminum | 5Y | $Al(NO_3)_3 \cdot 9H_2O$ | 10 | 3 | yes | - | 640 | 100% |
| 16 | zinc | 5Y | $Zn(NO_3)_2 \cdot 6H_2O$ | 20 | 2 | yes | - | - | |
| 17 | gallium | 5Y | $Ga(NO_3)_3 \cdot xH_2O$ | 20 | 2 | yes | - | - | |
| 18 | control | 5Y | - | - | - | - | - | 708 | 100% |
| 19 | aluminum zinc copper | 5Y | $Al(NO_3)_3 \cdot 9H_2O$ $Zn(NO_3)_2 \cdot 6H_2O$ $CuCl_2 \cdot 2H_2O$ | 40 20 0.05 | 2 | yes | - | 748 | 106% |
| 20 | control | 3Y | - | - | - | - | - | 1046 | 100% |
| 21 | aluminum copper | 3Y | $Al(NO_3)_3 \cdot 9H_2O$ $CuCl_2 \cdot 2H_2O$ | 10 0.05 | 2 | yes | - | 1117 | 107% |
| 22 | aluminum manganese | 3Y | $Al(NO_3)_3 \cdot 9H_2O$ $MnCl_2 \cdot 4H_2O$ | 10 0.03 | 2 | yes | - | 1082 | 103% |

COMPOSITION AND METHOD FOR GENERATING A SHADE GRADIENT IN ZIRCONIA DENTAL RESTORATION

CROSS REFERENCE TO RELATED APPLICATIONS

This application claims the benefit of U.S. Provisional Patent Application Ser. No. 62/644,761, filed on Mar. 19, 2018, and U.S. Provisional Patent Application Ser. No. 62/748,884, filed Oct. 22, 2018, both entitled "Composition and Method for Generating a Shade Gradient in Zirconia Dental Restoration," each of which is incorporated by reference in its entirety herein.

FIELD

This disclosure relates to compositions and methods for preparing dental restorations. More particularly, this disclosure relates to bleaching liquids of metal salts/complexes dissolved in a solvent for bleaching shaded dental zirconia.

BACKGROUND

Artificial teeth used in dental restorations are often made from ceramic material, such as zirconia. Zirconia, without special treatment, (i.e. unshaded zirconia) is unnaturally white for use in dental applications, and therefore must be colored to achieve a realistic appearance. There are several methods to color artificial teeth made from zirconia.

When unshaded zirconia blanks are used, units milled from the blanks require the addition of color to achieve realistic aesthetics. Dipping the milled units in a coloring liquid or brushing the coloring liquid on the surface of the milled units can generate shades in zirconia restorations. While the dipping method is simple, it results in monochromatically shaded zirconia. Though the brushing method can generate shade gradient in zirconia restorations, it requires a technician's extensive experience. Since absorption of coloring liquids varies depending on raw materials and the porosity of the zirconia blank, and other factors, shades achieved by the same coloring liquid in zirconia restorations can change from one blank to the next. A dental technician's proficiency, skill, and artistry also affect coloring consistency. When multi-unit bridges are colored by dipping in coloring solution, pontics absorb more colorants and show stronger chroma than crowns.

In contrast, pre-shaded blanks which are manufactured using pre-colored powder result in more consistent color of the restorations. Monochromatic pre-shaded zirconia blanks have been used to reduce the inconvenience of coloring with coloring liquids. However, monochromatic blanks cannot produce a shade gradient that natural teeth have.

Recently, multi-layer zirconia blanks have been produced by placing multiple layers of zirconia with different shades to create a multi-layered, gradient effect. Since the position of color change in the blank is fixed, positioning artificial teeth in the blank should be performed carefully. Even with careful positioning, the color gradient may not be consistent with natural teeth because, for example, heights of cusps in a tooth with multiple cusps are different. Producing multi-unit bridges is more difficult. Inspection of the correct positioning of the color gradient in the restoration before sintering is impossible because it is difficult, if not impossible, to assess the color of the unsintered blanks which do not show any gradient. Manufacture of multi-layer blanks requires more complex processes and equipment and a larger number of shaded powder batches than manufacture of monochromatic blanks.

Each of these techniques, and others, results in an unsintered "shaded zirconia."

Easy control of color gradient in shaded zirconia is desirable. Simple bleaching of shaded zirconia makes the use of shaded zirconia, regardless of source, more universal because shades can be customized by applying the bleaching solution where color gradient is required.

Currently, a liquid, Nacera Blue X, that can bleach color of porous pre-shaded zirconia units is available in the market. The Blue X is a solution of yttrium nitrate. When the Blue X is brushed on pre-shaded zirconia, the color is bleached. However, more yttria doping to yttria-stabilized zirconia makes zirconia more stabilized. The treated area has more cubic phase than non-treated area, which results in decrease of strength and toughness. The decrease of strength is large enough to change a class of zirconia in dental applications. In addition, the treated dental restorations or structure warp upon sintering. Gradient of shrinkage may generate noticeable warping, especially in longer bridges. Warping is a critical problem in multi-unit bridges. There are two causes. Shrinkage rates of the cubic phase and the tetragonal phase are different. Also, addition of high concentrated yttrium nitrate solution, which is required to have strong enough bleaching effect, has an effect of filling the existing porous structure with extra materials, i.e., increase of density, which causes less shrinkage in the applied area than untreated area.

EP3132788A1 claims that addition of stabilizers of zirconia such as yttria, magnesia, calcia, and ceria to pre-shaded yttria stabilized zirconia increases translucency and bleaches colors. (Yttria, magnesia, calcia, and ceria are the oxides of yttrium, magnesium, calcium, and cerium, respectively, as will be known to those of ordinary skill in the art.) Addition of extra yttria to yttria-stabilized zirconia results in increase of the cubic phase. Increase in translucency results from the increase of cubic phase. But, co-doping of other stabilizers does not always result in increase of cubic phase. In many cases, it causes not only decrease of translucency, but also decrease of strength.

ISO 6872:2015 is a recognized international standard which specifies the requirements and corresponding test methods for dental ceramic materials for fixed all-ceramic restorations and prostheses. The standard divides ceramics into five classes according to their intended clinical use and sets forth the required mechanical properties for each class, one being flexural strength. Current all-ceramic zirconia restorations generally fall into classes four and five. The use of class four ceramics in a monolithic restoration is limited to a 3 unit bridge, while class five ceramics may be used for 4 units or greater. The minimum flexural strengths for class four and class five ceramics are 500 MPa and 800 MPa, respectively. The application of certain color shading and bleaching liquids to these ceramics have been shown to materially reduce the flexural strength and the class of the resulting restorations. It would generally be undesirable to reduce the flexural strength of a class four or class five ceramic such that it no longer maintains its class and intended use.

The following characteristics are desirable for a bleaching liquid: 1. has no or small effect on strength to maintain the class of the material; 2. does not act as a colorant in zirconia. Though it is not desirable for the bleaching component in the liquid to have a color, the bleaching effect can be combined with other coloring liquid to enhance features of teeth, for example enamel effect by adding additional colorants to make the incisal area look more translucent.

Described herein are compositions and methods which allow for simple bleaching, and optionally coloring, of unsintered shaded zirconia, whether derived from unshaded zirconia dipped in a coloring liquid, monochromatic pre-shaded zirconia, or other technique.

SUMMARY

Some embodiments provide a liquid for bleaching a shaded dental zirconia, the liquid comprising a metal compound dissolved in a solvent.

In some embodiments, the metal compound comprises one or more metal selected from zinc, gallium, and aluminum.

In some embodiments, the metal compound is a metal salt or complex comprising a metal and a counterpart selected from halides (Cl, F, Br, and I), nitrate, acetate, sulfate, lactate, propionate, formate, and alkoxides.

In some embodiments, the metal is selected from zinc, gallium, and aluminum. In some embodiments solid salts or complexes of zinc, aluminum, and gallium are present at about 0.1 wt % to about 80 wt % by weight of the bleaching liquid. When liquid metal compounds of zinc, aluminum, and gallium are used, the liquid metal compound is present at about 0.1 wt % to about 100 wt % of the bleaching liquid.

In some embodiments, the metal salt or metal complex is selected from:

| salt/complex | Conc. (wt %) |
|---|---|
| $ZnCl_2$ | 1-80 |
| $Zn(NO_3)_2 \cdot 6H_2O$ | 1-80 |
| $Ga(NO_3)_3 \cdot xH_2O$ | 1-80 |
| $Al(NO_3)_3 \cdot 9H_2O$ | 1-80 |

In some embodiments, the liquid further comprises at least one coloring agent.

Some embodiments provide a method of bleaching a shaded dental blank, the method comprising applying at least one coat of a liquid as described herein.

These and other embodiments will be readily apparent to one of ordinary skill in the art upon reading this disclosure, which is meant to be illustrative in nature.

BRIEF DESCRIPTION OF THE DRAWINGS

FIG. 2 is a table showing the composition of the various examples and comparative examples and results.

DETAILED DESCRIPTION

Figure 1:
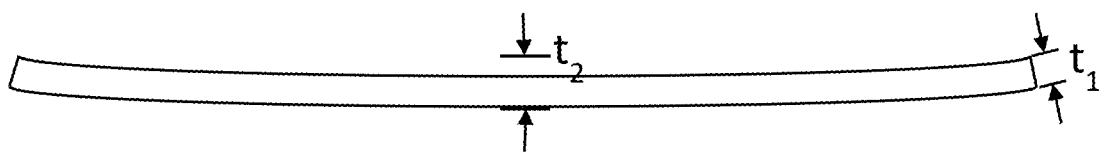
FIG. 1 is a graphic depicting how warpage is measured.
Figure 3:
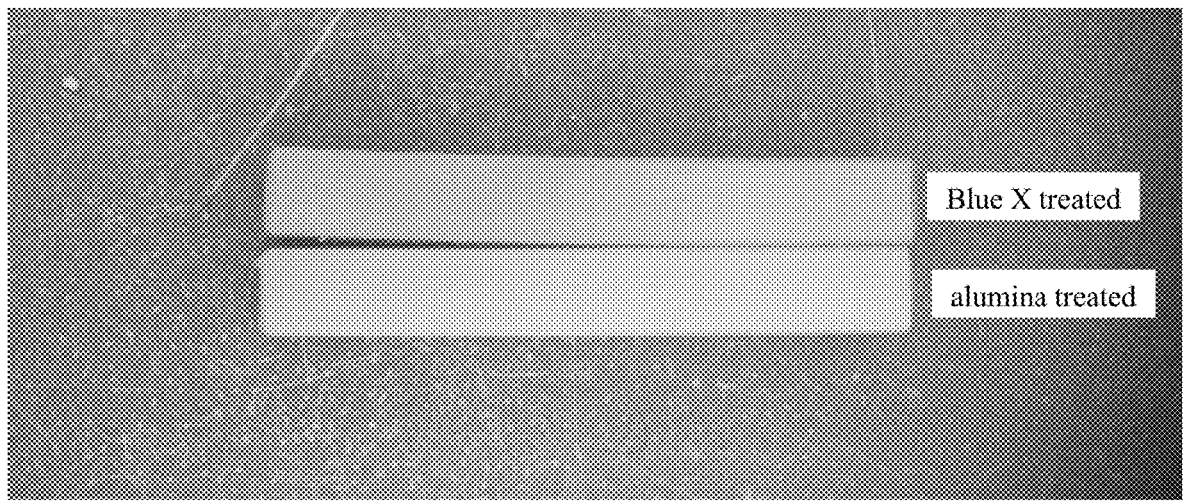
FIG. 3 is a photo comparing various examples.
Figure 4:
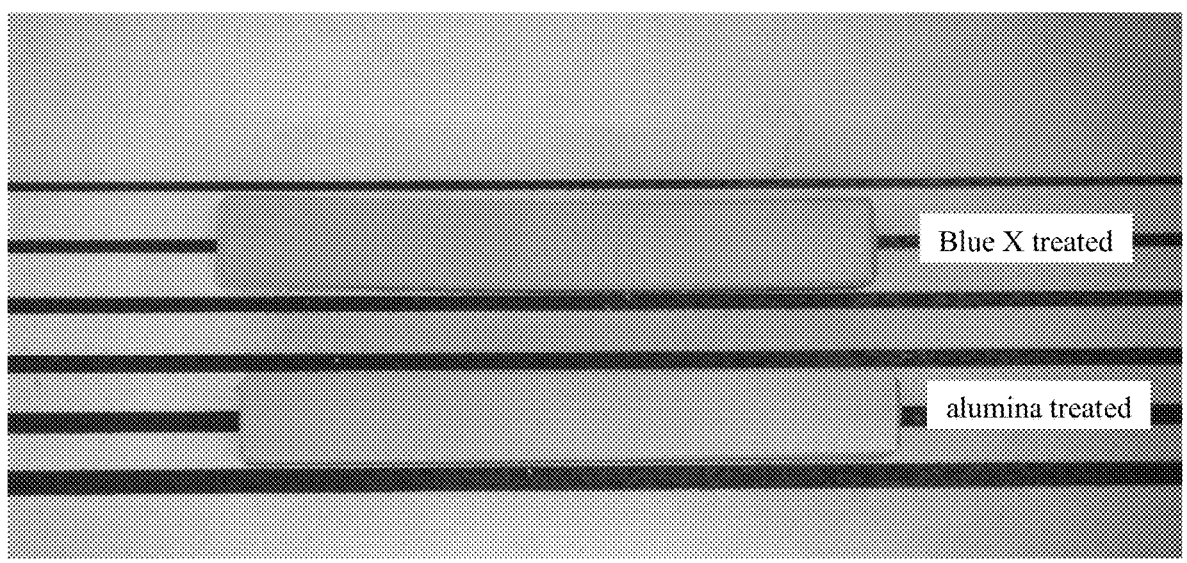
FIG. 4 is a photo comparing various examples.

Compositions and methods for bleaching and optionally coloring unsintered, shaded zirconia, such as but not limited to pre-shaded zirconia or colored but previously unshaded zirconia, are disclosed herein. Simple bleaching of shaded zirconia makes the use of shaded zirconia, regardless of source, more universal because shade can be customized by applying the bleaching solution where color gradient is required.

The following characteristics are desirable for a bleaching liquid: 1. has no or small effect on strength to maintain the class of the material; 2. does not act as a colorant in zirconia. Though it is not desirable for the bleaching component in the liquid to have a color, the bleaching effect optionally can be combined with other coloring liquid to enhance features of teeth, for example enamel effect by adding additional colorants to make incisal area look more translucent.

Bleaching liquids were made by solving solid or liquid metal compounds in solvents.

The metal is believed to drive the compounds bleaching ability. Some metal compounds exist as liquid. Liquid metal compounds can be used with or without dilution with the solvents.

In some embodiments, the metal is selected from zinc, gallium, and aluminum. In some embodiments, the metal is present as a dissolved solid salt or complex. Particularly, salts or complexes of halogens, particularly chlorides, nitrates ($NO_3$), and $NO_3$ hydrates are useful in the compositions described herein. The salts or complexes are present at about 0.1 wt % to about 80 wt % by weight of the bleaching liquid. In some embodiments, the metal compound is present at 1%, 5%, 10%, 20%, 30%, 40%, 50%, 60%, 70%, 80% or any value or range of values between any two of these. When liquid metals are used, the liquid metal compound is present at about 0.1 wt % to about 100 wt % of the bleaching liquid. In some embodiments, the metal compound is present at 1%, 5%, 10%, 20%, 30%, 40%, 50%, 60%, 70%, 80%, 90%, 100% or any value or range of values between any two of these.

In some embodiments, the metal is selected from zinc, gallium, and aluminum. In some embodiments, solid salts or complexes of zinc, aluminum, and gallium are present at about 0.1 wt % to about 80 wt % by weight of the bleaching liquid. In some embodiments, the metal compound is present at 1%, 5%, 10%, 20%, 30%, 40%, 50%, 60%, 70%, 80% or any value or range of values between any two of these. When liquid metal compounds of zinc, aluminum, and gallium are used, the liquid metal compound is present at about 0.1 wt % to about 100 wt % of the bleaching liquid. In some embodiments, the metal compound is present at 1%, 5%, 10%, 20%, 30%, 40%, 50%, 60%, 70%, 80%, 90%, 100% or any value or range of values between any two of these.

In some embodiments, the metal compound is a metal salt or complex comprising a metal and a counterpart selected from halides (Cl, F, Br, and I), nitrate, acetate, sulfate, lactate, propionate, formate, and alkoxides.

Solvents can be water and/or any organic solvent such as methanol, ethanol, propanol, isopropanol, ethyl acetate, hexane, toluene, etc., and mixture of these solvents as long as the salt and/or complex are soluble in the solvents. The solvents are not limited to the solvents listed above.

Bleaching power of the bleaching liquids depends on metal in the bleaching liquid, type of the zirconia and how shading was performed. In 3Y and 4Y zirconia, bleaching liquids shows strong effect, but 5Y zirconia requires higher concentration of metal compounds for strong enough bleaching. Pre-shaded zirconia readily absorbs bleaching liquid, so the bleaching is more effective. In contrast, unshaded zirconia shaded by coloring liquid does not absorb bleaching liquid as much as pre-shaded zirconia unless the unshaded zirconia is thoroughly dried after shading. The preferred concentration range of metal compounds in the bleaching liquid for each case is:

| Type of zirconia | Shading* | Preferred concentration range of metal compound |
| --- | --- | --- |
| 3Y/4Y | Unshaded/user-shaded | 3-30 wt % |
| | pre-shaded | 3-30 wt % |
| 5Y | Unshaded/user-shaded | 15-80 wt % |
| | pre-shaded | 10-40 wt % |

When more than one metal compound is present in the bleaching liquid, the concentration indicates the total concentration of the metal compounds. In some zirconia, yttrium concentration falls between 4Y and 5Y. The preferred concentration can be changed accordingly.

The solution may contain viscosity modifier to control penetration depth of the solutions. The viscosity modifiers are glycerol, polyethylene glycol (PEG), polyacylic acid (PAA) and its salts, polyvinylalcohol (PVA), polymethacrylic acid (PMAA) and its salts, polyvinylpyrrolidone (PVP), etc., and mixture of these chemicals. The viscosity modifiers are not limited to the substances listed above.

Acid may be dissolved in the solution to enhance solubility of the metal compounds or stability of the solutions. Dye may be added to the solution as a marker to distinguish applied area from unapplied area.

Bar shaped samples were milled for a flexural strength test from pre-shaded zirconia blanks. Metal compound solutions were applied to one side of the bars by brushing. In some examples, solutions contain copper or a manganese compound which is added as a coloring agent for enamel effect. Sintering was done at 1530° C. for 2 hours for 3Y zirconia and at 1450° C. for 2 hours for 5Y zirconia. The final dimensions of sintered bars were about 30 mm in length, 4 mm in width, and 3 mm in thickness. Flexural strength test was performed using a three-point bending setup. Unless any description is provided, 16 samples of each group were tested for strength measurement. The treated side was placed downward to make the treated side under tensile stress. Warping was quantified by percent increase of thickness from original thickness, $t_1$, to warped thickness, $t_2$, as depicted in FIG. 1.

EXAMPLES

As a control, bars were prepared from a pre-shaded 3Y zirconia blank without any treatment.

Bars prepared from a pre-shaded 3Y zirconia blank were treated with two coats of Nacera Blue X solution which contains 50-70 wt % yttrium nitrate hexahydrate.

Bars prepared from a pre-shaded 3Y zirconia blank were treated with two coats of 50 wt % magnesium chloride hexahydrate solution.

Bars prepared from a pre-shaded 3Y zirconia blank were treated with two coats of 10 wt % zinc chloride solution.

Bars prepared from a pre-shaded 3Y zirconia blank were treated with two coats of 10 wt % zinc nitrate hexahydrate solution.

Bars prepared from a pre-shaded 3Y zirconia blank were treated with two coats of 40 wt % ytterbium nitrate pentahydrate solution.

Bars prepared from a pre-shaded 3Y zirconia blank were treated with two coats of 40 wt % gadolinium nitrate hexahydrate solution.

Bars prepared from a pre-shaded 3Y zirconia blank were treated with two coats of 40 wt % lanthanum nitrate hexahydrate solution.

Bars prepared from a pre-shaded 3Y zirconia blank were treated with two coats of 10 wt % gallium nitrate hydrate solution.

Bars prepared from a pre-shaded 3Y zirconia blank were treated with one coat of 10 wt % aluminum nitrate nonahydrate solution.

Bars prepared from a pre-shaded 3Y zirconia blank were treated with two coats of 10 wt % aluminum nitrate nonahydrate solution.

Bars prepared from a pre-shaded 3Y zirconia blank were treated with three coats of 10 wt % aluminum nitrate nonahydrate solution.

As a control, bars were prepared from an unshaded 5Y zirconia blank without any treatment.

Bars prepared from an unshaded 5Y zirconia blank were treated with two coats 10 wt % aluminum nitrate nonahydrate solution. These unshaded bars were used for flexural strength test. Bars prepared from a pre-shaded 5Y zirconia blank were treated with two coats 10 wt % aluminum nitrate nonahydrate solution for bleaching test.

Bars prepared from an unshaded 5Y zirconia blank were treated with three coats of 10 wt % aluminum nitrate nonahydrate solution. These unshaded bars were used for flexural strength test. Bars prepared from a pre-shaded 5Y zirconia blank were treated with three coats of 10 wt % aluminum nitrate nonahydrate solution for bleaching test.

Bars prepared from an unshaded 5Y zirconia blank were treated with two coats of 20 wt % zinc nitrate hexahydrate solution.

Bars prepared from an unshaded 5Y zirconia blank were treated with two coats of 20 wt % gallium nitrate hydrate solution.

As a control, bars prepared from an unshaded 5Y zirconia blank were dipped in A4 coloring liquid and dried.

Bars prepared from an unshaded 5Y zirconia blank were dipped in A4 coloring liquid and dried at 70° C. for 30 minutes. The bars were treated with two coats of a solution containing 40 wt % aluminum nitrate nonahydrate, 20 wt % zinc nitrate hexahydrate, and 0.05 wt % cupric chloride dihydrate.

As a control, bars were prepared from a pre-shaded 3Y zirconia blank without any treatment.

Bars prepared from a pre-shaded 3Y zirconia blank were treated with two coats of a solution containing 10 wt % aluminum nitrate nonahydrate and 0.05 wt % cupric chloride dihydrate.

Bars prepared from a pre-shaded 3Y zirconia blank were treated with two coats of a solution containing 10 wt % aluminum nitrate nonahydrate and 0.03 wt % manganese chloride tetrahydrate.

FIG. 2 is a table listing the experimental conditions and results. It can be seen from the results that use of the metals salts or metal complexes disclosed herein reduces warpage, without negatively affecting flexural strength, and thus without reducing the class of the material.

Though any metal compounds that have bleaching effect on the Table in FIG. 2 can be used for bleaching liquids, there are some limitations. According to ISO 6872, class 5 materials have flexural strength of at least 800 MPa. (Notably, ytterbium, gadolinium, and lanthanum did not exhibit meaningful bleaching effect.) 3Y zirconia is a class 5 material. However, the samples treated with yttrium nitrate hexahydrate (Blue X solution, example 2) and magnesium chloride hexahydrate (example 3) showed flexural strength lower than 800 MPa. The class of the material changed to a lower level. The decrease of flexural strength due to co-doping of stabilizers to yttria-stabilized zirconia limits usage of the materials down to 3 unit bridges. Other bleaching liquids containing zinc, gallium, or aluminum salts have no considerable decrease of flexural strength; in some instances, an increase in flexural strength was seen. This means no class change of 3Y zirconia materials. Considering bleaching effect, warping, and flexural strength, compounds of aluminum, zinc, and gallium are proper to be used as bleaching liquid of shaded zirconia, even in multi-unit bridges.

We claim:

1. A method of generating a color gradient by bleaching a pre-shaded zirconia, the method comprising:
    applying, to the pre-shaded zirconia, a liquid comprising a metal compound or metal compounds comprising one or more metal selected from zinc, gallium, and aluminum in an amount sufficient to cause bleaching by the formation of oxides in the pre-shaded zirconia after sintering at a temperature greater than or equal to 1450° C., and optionally solvent,
    wherein the liquid reduces the intensity of color in the pre-shaded zirconia, and
    wherein the liquid substantially maintains the flexural strength of the pre-shaded zirconia.

2. The method of claim 1, wherein the metal compound is a metal salt or complex comprising a metal and a counterpart selected from halides (Cl, F, Br, and I), nitrate, acetate, sulfate, lactate, propionate, formate, and alkoxides.

3. The method of claim 1, wherein the metal compound is a solid salt or complex of zinc, aluminum, or gallium and is present at about 0.1 wt % to about 80 wt % by weight of the bleaching liquid.

4. The method of claim 1, wherein the metal compound is a liquid metal compound of zinc, aluminum, or gallium and is present at about 0.1 wt % to about 100 wt % of the bleaching liquid.

5. The method of claim 1, wherein the metal is selected from zinc, gallium, and aluminum.

6. The method of claim 2, wherein the metal salt or complex is selected from:

| salt/complex | Conc. (wt %) |
|---|---|
| $ZnCl_2$ | 1-80 |
| $Zn(NO_3)_2 \cdot 6H_2O$ | 1-80 |
| $Ga(NO_3)_3 \cdot xH_2O$ | 1-80 |
| $Al(NO_3)_3 \cdot 9H_2O$ | 1-80 |

* * * * *